United States Patent [19]

Muchowski et al.

[11] Patent Number: 5,082,951
[45] Date of Patent: Jan. 21, 1992

[54] PROCESS FOR PREPARING 5-AROYL-2,3-DIHYDRO-1H-PYRROLIZINE-1,1-DICARBOXYLATES (I) AND INTERMEDIATES THEREFOR

[75] Inventors: Joseph M. Muchowski, Sunnyvale; In-Seop Cho, Mountain View, both of Calif.

[73] Assignee: Syntex (U.S.A.) Inc., Palo Alto, Calif.

[21] Appl. No.: 596,843

[22] Filed: Oct. 12, 1990

[51] Int. Cl.$^5$ ................ C07D 487/04; C07D 207/337
[52] U.S. Cl. ..................................... 548/453; 548/539
[58] Field of Search ............................... 548/539, 453

[56] References Cited

U.S. PATENT DOCUMENTS

| | | | |
|---|---|---|---|
| 4,089,969 | 5/1978 | Muchowski et al. | 424/274 |
| 4,347,185 | 8/1982 | Muchowski et al. | 260/326.25 |
| 4,347,186 | 8/1982 | Muchowski et al. | 548/516 |
| 4,347,187 | 8/1982 | Muchowski et al. | 548/516 |
| 4,353,829 | 10/1982 | Thurber et al. | 260/326.25 |
| 4,873,340 | 10/1989 | Muchowski et al. | 548/453 |

OTHER PUBLICATIONS

A Citterio et al., Tet. Lett., 30 (10), 1289-1292 (1989)., "Oxidative Deprotonation of Carbonyl Compounds by Fe(III) Salts".
A. Citterio et al., J. Org. Chem., 54, 2713-2718 (1989), "Manganese (III) Acetate Induced Cyclization . . . ".
J. White et al., J. Org. Chem., 42(26), 4248-4251 (1977), "The Vilsmeier-Haack Aroylation of Pyrroles Reexamined".
C. Gonzalez et al., Can. J. Chem., 61, 1697-1702 (1983), "Protecting Groups for the Pyrrole Nitrogen Atom . . . ".
E. I. Heiba et al., Org. Syn., 61, 22-24, "Substituted $\gamma$-Butyrolactones from Carboxylic Acids . . . ".
J. D. McClure, J. Org. Chem., 27, 2365-2368 (1962), "Synthesis of Spirouundecatrienones . . . ".
N. Kornblum et al., J. Am. Chem. Soc., 81, 4113-4114 (1959), "A New and Selective Method of Oxidation . . . ".
L. B. Levy, J. Org. Chem., 54, 253-254 (1989), "Facile Oxidation of Manganese (II) . . . ".
C. Walling, Accts. Chem. Res., 8, 125-131 (1975), "Fenton's Reagent Revisited".
H. C. Braun et al., Angew. Chem. Internat. Ed., 11(8), 692-700 (1972), "Organic Syntheses via Free-Radical Displacement Reactions . . . ".

Primary Examiner—David B. Springer
Attorney, Agent, or Firm—Derek P. Freyberg

[57] ABSTRACT

5-Aroyl-2,3-dihydro-1H-pyrrolizine-1,1-dicarboxylates of the formula

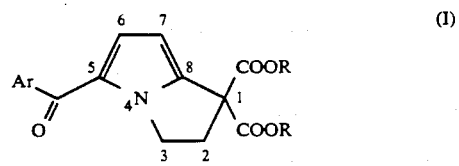

are prepared from 2-aroylpyrroles. Hydrolysis and mono-decarboxylation of these compounds affords ketorolac and related compounds.

13 Claims, No Drawings

PROCESS FOR PREPARING 5-AROYL-2,3-DIHYDRO-1H-PYRROLIZINE-1,1-DICARBOXYLATES (I) AND INTERMEDIATES THEREFOR

CROSS-REFERENCE TO RELATED APPLICATION

This application is related to the subject matter of our copending and commonly assigned U.S. Pat. application Ser. No. 07/596,802, filed Oct. 12, 1990 for "A Process for preparing 5-Aroyl-2,3-Dihydro-1H-Pyrrolizine-1,1-Dicarboxylates (II)", which is incorporated herein by reference.

BACKGROUND OF THE INVENTION

Field of the Invention

This invention provides novel processes for preparing substituted pyrrolizine compounds. More particularly, this invention provides processes for the preparation of 5-aroyl-2,3-dihydro-1H-pyrrolizine-1,1-dicarboxylates (I)

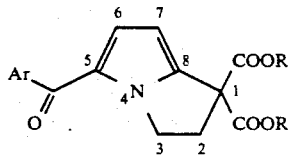

from 2-aroylpyrroles. Hydrolysis and monodecarboxylation of compound of formula I affords ketorolac and related compounds.

BACKGROUND TO THE INVENTION

5-Aroyl-2,3-dihydro-1H-pyrrolizine-1-carboxylic acids (II), and the pharmacologically acceptable salts and esters thereof, are now under study

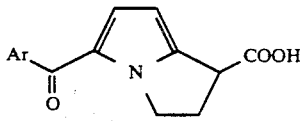

as analgesic, anti-inflammatory, and anti-pyretic agents for mammals, including man. They are also smooth muscle relaxants.

Two exemplary compounds under clinical study in man are ketorolac, 5-benzoyl-2,3-dihydro-1H-pyrrolizine-1-carboxylic acid, (II, Ar=C$_6$H$_5$) which is currently being marketed in the United States, Italy, Holland, and New Zealand, and anirolac, 5-p-anisoyl-2,3-dihydro-1H-pyrrolizine-1-carboxylic acid, (II, Ar=p-CH$_3$O-C$_6$H$_5$), both disclosed in U.S. Pat. No. 4,089,969 (Muchowski et al., assigned to Syntex (U.S.A.) Inc.). Other compounds, where the 5-aroyl substituents are substituted or unsubstituted benzoyl, furoyl, thenoyl, and pyrroyl, and where the 6- and/or 7-position on the pyrrolizine nucleus is optionally substituted by lower alkyl or halogen, and uses thereof, are also disclosed in a series of patents assigned to Syntex (U.S.A.) Inc., beginning with U.S. Pat. No. 4,089,969, and including U.S. Pat. Nos. 4,087,539; 4,097,579; 4,140,698; 4,232,038; 4,344,943; 4,347,186; 4,458,081; 4,347,187; 4,454,326; 4,347,185; 4,505,927; 4,456,759; 4,353,829; 4,397,862; 4,457,941; and 4,454,151. U.S. Pat. Nos. 4,511,724 and 4,536,512, assigned to Merck & Co., Inc., disclose 5-(substituted pyrrol-2-oyl)-2,3-dihydro-1H-pyrrolizine-1-carboxylic acid derivatives and 5-(2,3-dihydro-1H-pyrrolizine-2-oyl)-2,3-dihydro-1H-pyrrolizine-1-carboxylic acid derivatives, respectively.

Various methods for the preparation of these pyrrolizines are exemplified in the patent and chemical literature.

For example, U.S. Pat. Nos. 4,347,186; 4,458,081; 4,347,187; and 4,454,326 disclose the preparation of 5-aroyl-pyrrolizines from pyrroles, and certain intermediates, by the following route

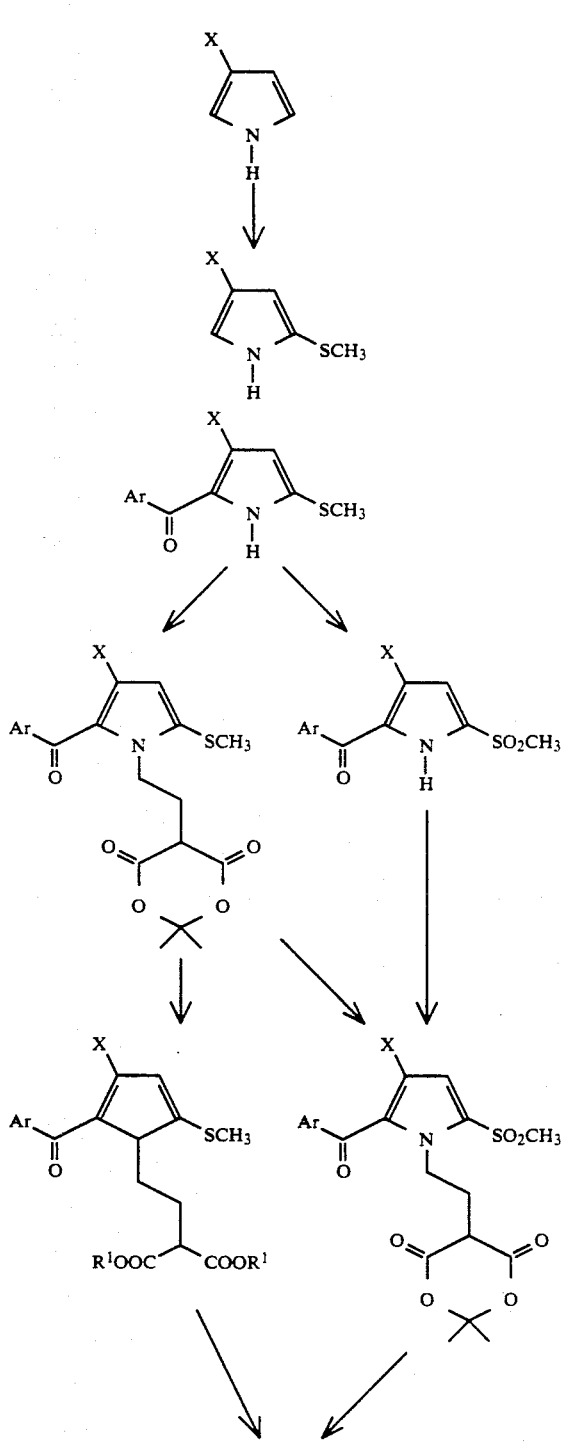

-continued

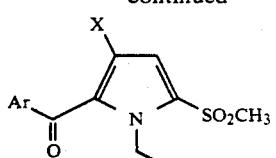

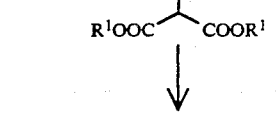

wherein:

R¹ and X are independently hydrogen or lower alkyl; and

Ar is a moiety selected from the group consisting

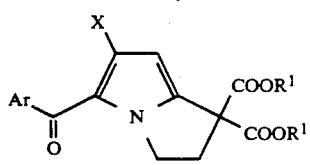

in which:

R² is hydrogen, methyl, chloro, or bromo, the R² substitution being at the 3-, 4- or 5-position of the ring;

R³ is hydrogen, lower alkyl, lower alkoxycarbonyl, lower alkylcarbonyl, fluoro, chloro or bromo, the R³ substitution being at any available position in the ring;

R⁴ is hydrogen or lower alkyl; and

Y is oxygen or sulfur.

U.S. Pat. Nos. 4,347,185; 4,505,927; and 4,456,759 disclose the preparation of 5-aroyl-pyrrolizines from pyrroles, and certain intermediates, by the following route:

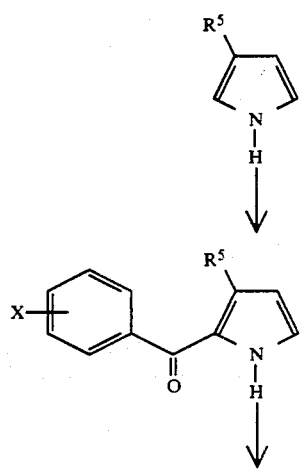

-continued

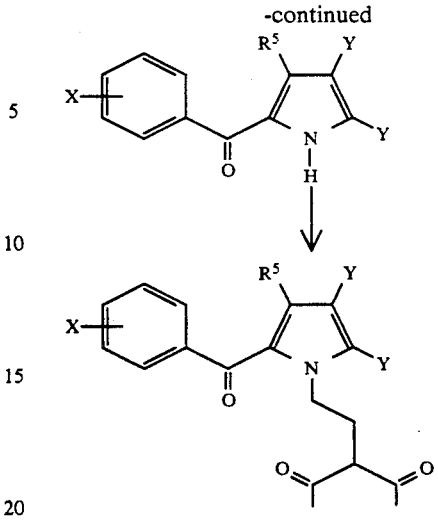

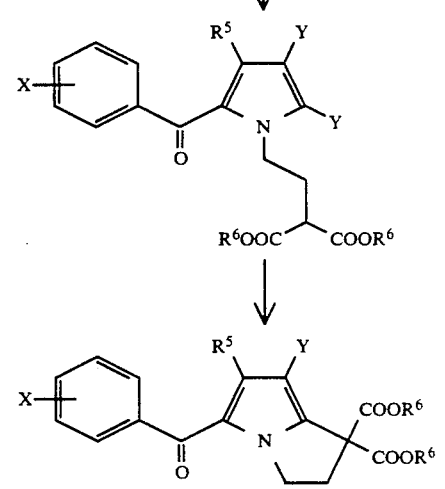

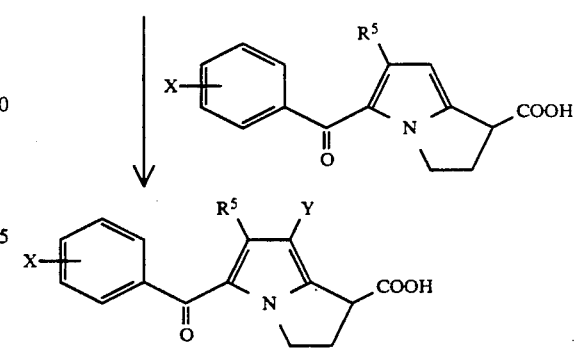

wherein:

$R^5$ is hydrogen or lower alkyl;

$R^6$ is lower alkyl;

X is hydrogen, lower alkyl, lower alkoxyl, lower alkoxycarbonyl, carboxyl, lower alkylcarbonyl, sulfonic acid, sulfonic acid alkyl ester, fluoro, chloro, or bromo; and Y is chloro or bromo.

U.S. Pat. No. 4,873,340, issued Oct. 10, 1989, discloses the preparation of 5-aroyl-2,3-dihydro-1H-pyrrolizine-1,1-dicarboxylates from 2-halopyrroles, and certain intermediates, by the following route:

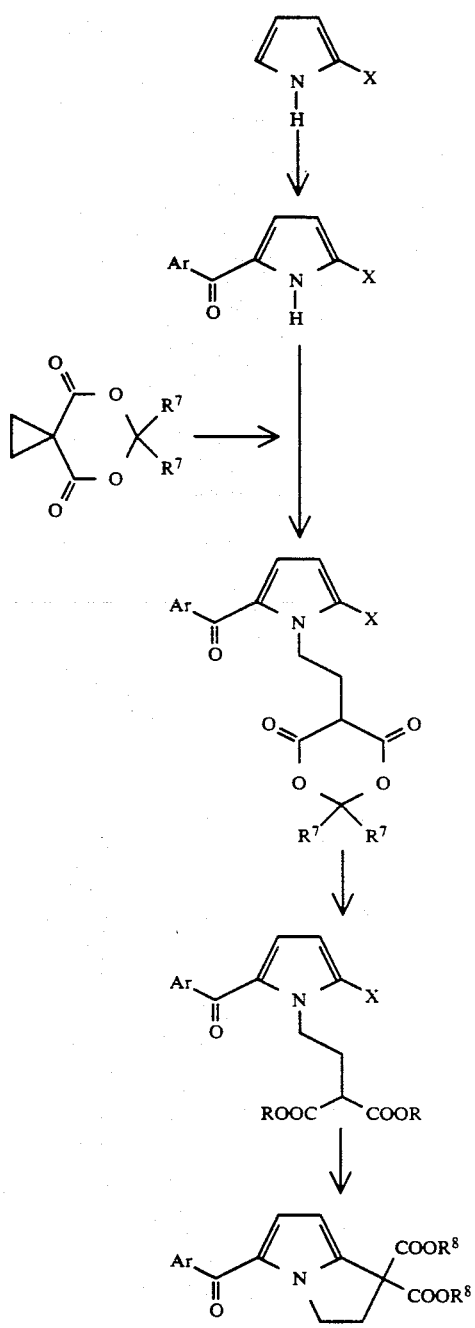

in which
R[8] is lower alkyl;
Ar is an aryl group which does not contain nitrogen that is substituted with a hydrogen; and
each R[7] is independently lower alkyl; and
X is bromo or chloro.

It has recently been reported that iron(III) salts and manganese(III) acetate can induce the oxidative radical cyclization of β-dicarbonyl moieties to form homocyclic aromatic systems. A. Citterio, et al., *Tetrahedron Letters*, 30, 1289 (1989); *J. Org. Chem.*, 54, 2713 (1989).

The disclosures of these patents and literature articles and other patents and articles referred to throughout this application are incorporated herein by reference.

SUMMARY OF THE INVENTION

In a first aspect, this invention provides a novel process for the preparation of 5-aroyl-2,3-dihydro-1H-pyrrolizine-1,1-dicarboxylates (I)

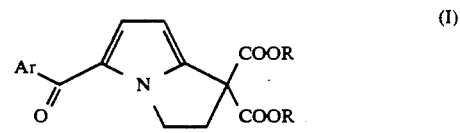

in which

R is lower alkyl; and

Ar is an aryl group, which does not contain any nitrogen that is substituted with hydrogen; from 2-aroylpyrroles via two alternative radical cyclizations.

The preparation may be represented schematically:

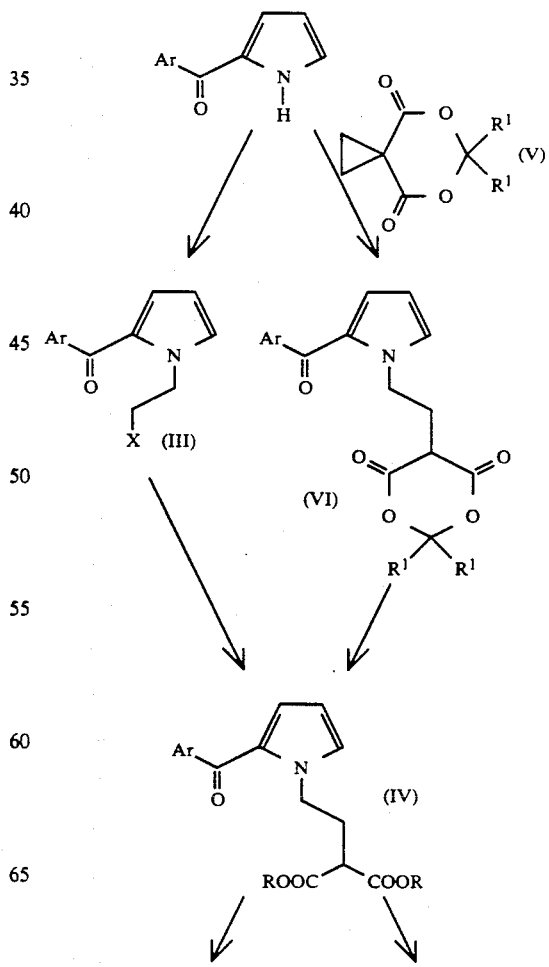

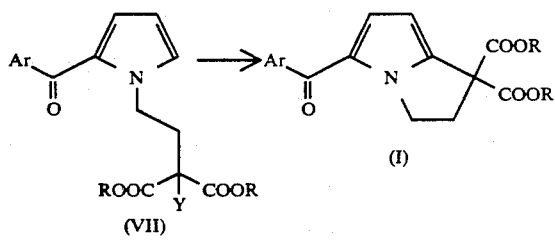

in which

R and Ar are as previously defined;

each R' is independently lower alkyl;

X is selected from the group consisting of bromo, iodo, arenesulfonyloxy; and

Y is selected from the group consisting of bromo or iodo.

In a second aspect, this invention provides a preparation of 5-aroyl-2,3-dihydro-1H-pyrrolizine-1-carboxylic acids and their pharmaceutically acceptable salts by the preparation of compound of formula I by the processes described above, followed by hydrolysis and monodecarboxylation thereof, optionally followed by salt formation.

In a third aspect, this invention provides novel compounds of formulae IV and VII, wherein R, Y, and Ar are as described above, which are useful as intermediates in the processes herein.

DETAILED DESCRIPTION OF THE INVENTION

Definitions and General Parameters

Unless otherwise stated, the following terms used in the specification and claims have the meanings given below:

"Alkyl", denoted generally by R, e.g., by $R^1$ or $R^2$, refers to straight or branched chain aliphatic groups having 1-12 carbon atoms, or aliphatic groups having 3-12 carbon atoms and containing at least one cyclic aliphatic group (cycloalkyl group). Those alkyl groups having 1-8 carbon atoms, and especially those having 1-4 carbon atoms, are presently preferred. The cycloalkyl groups having 3-8 carbon atoms are presently preferred. Alkyl groups include those exemplified by methyl, ethyl, cyclopropyl, cyclopropylmethyl, secbutyl, heptyl, and dodecyl. All of the above can either be unsubstituted or substituted with one or more non-interfering sustituents, e.g., halogen; $C_1$-$C_4$ alkoxy; $C_1$-$C_4$ acyloxy; formyl; alkylenedioxy: benzyloxy; phenyl or benzyl, each optionally substituted with from 1 to 3 substituents selected from halogen, $C_1$-$C_4$ alkoxy or $C_1$-$C_4$ acyloxy. The term "non-interfering" characterizes the substituents as not adversely affecting any reactions to be performed in accordance with the process of this invention. If more than one alkyl group is present in a given molecule, each may be independently selected from "alkyl" unless otherwise stated. Preferred alkyl groups are $C_1$-$C_4$ alkyl, and particularly preferred are methyl and ethyl.

"Lower alkyl" refers to an alkyl group of one to six carbon atoms. Lower alkyl groups include those exemplified by methyl, ethyl, n-propyl, i-propyl, n-butyl, t-butyl, i-butyl (2-methylpropyl), cyclopropylmethyl, i-amyl, n-amyl and hexyl. Preferred lower alkyls are methyl and ethyl. If more than one alkyl group is present in a given molecule, each may be independently selected from "lower alkyl" unless otherwise stated.

"Lower alkenyl" refers to a branched or unbranched singly ethylenically unsaturated hydrocarbon chain containing from two to six carbon atoms. Lower alkenyl groups include those exemplified by ethenyl (vinyl), propenyl, and butenyl.

"Lower alkynyl" refers to a branched or unbranched singly acetylenically unsaturated hydrocarbon chain containing from two to six carbon atoms. Lower alkynyl groups include those exemplified by ethynyl (acetylenyl), propynyl, and butynyl.

"Lower alkoxide", "lower alkanol", "lower alkylamine", "lower alkyl ester", "lower alkanoic acid", and similar terms refer to alkoxides, alkanols, alkylamines, alkyl esters, alkanoic acids, etc., in which the (or each) alkyl group is a "lower alkyl" as defined above.

"Alkyl radical" refers to an alkyl group which possesses at least one unpaired electron. Alkyl radicals include those exemplified by $CH_3\cdot$, $\cdot CH_2CH_3$, and the like.

"Aryl", denoted by Ar, includes monocyclic or condensed carbocyclic and heterocyclic aromatic groups having from 6 to 20 carbon atoms and up to three hetero atoms. Aryl groups include those exemplified by phenyl, naphthyl, furyl, thienyl, pyrrolyl, carbazolyl, and benzoxazolyl. These groups may be substituted with one or more non-interfering substituents, e.g., those selected from lower alkyl; lower alkenyl; lower alkynyl; lower alkoxy; lower alkylthio; lower alkylsulfinyl; lower alkylsulfonyl, dialkylamine; halogen; hydroxy; phenyl; phenyloxy; benzyl; benzoyl; and nitro. Each substituent may be optionally substituted with additional non-interfering substituents. Preferred aryl groups include, for example, those selected from the group consisting of in which

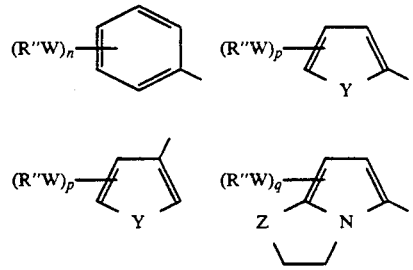

R" is hydrogen, fluoro, chloro, bromo or nitro, or lower alkyl, lower alkenyl, or lower alkynyl, optionally substituted by halogen;

W is a covalent bond, —O—, —S—, —S(O)—, —S(O)$_2$—, —NR—, —CHR—, where R is alkyl; except that if R" is nitro, fluoro, chloro, or bromo, then W is a covalent bond;

Y is —O—, —S—, or —NR—, with R being as defined above;

Z is —O—, —S—, —S(O)—, —S(O)$_2$—, —NR"—, or —CHR"—;

n is 0 to 5;

p is 0 to 3; and q is 0 to 2;

A particularly preferred aryl group is selected from 4-(R"W)-phenyls, especially phenyl, 4-methoxyphenyl, 4-methylthiophenyl, and 4-vinylphenyl.

"Aroyl" refers to the group —C(O)—Ar, where Ar is an aryl group.

"Alkoxycarbonyl" refers to the group —C(O)OR", where R" is lower alkyl.

"Arenesulfonyloxy" refers particularly to the group —OSO$_2$Ar, where Ar is aryl, such as benzenesulfonyloxy and p-tolueneslfonyloxy, but also includes other equivalent alkylsulfonyloxy groups such as methanesulfonyloxy, ethanesulfonyloxy, and the like.

"Pharmaceutically acceptable salts" refer to those salts which retain the biological effectiveness and properties of the free acids and which are not biologically or otherwise undesirable, formed with alkali metal bases such as sodium or potassium; alkaline earth metal bases such as calcium; and with organic bases such as tromethamine, diethylamine, ethanolamine, piperidine, isopropylamine, choline, caffeine, and the like.

"Protic polar solvent" includes organic solvents such as methanol, ethanol, acetic acid, and the like.

"Aprotic polar solvent" includes organic solvents which may be either water-immiscible, such as halogenated hydrocarbons, e.g., methylene chloride, chloroform, and the like, or water-miscible, such as tetrahydrofuran, dimethoxyethane, dimethylformamide, dimethylsulfoxide, and the like.

"Nonpolar solvent" includes organic solvents such as benzene, toluene, carbon tetrachloride, and ligroin.

"Alkanoic acid" refers to an organic acid of the formula RCOOH where R is an alkyl group of one to ten carbon atoms.

"Strong mineral acid" refers to an inorganic, water-soluble, easily dissociable Bronsted-Lowry acid, such as hydrochloric, sulfuric, phosphoric acids and the like.

"Strong base" refers to bases such as alkali metal hydroxides, alkali metal alkoxides, alkali metal hydrides, alkali metal di(lower alkyl)amines, and the like, for example, sodium hydroxide, potassium methoxide, sodium hydride, lithium di(isopropyl)amine, and the like.

"Weak base" refers to bases such as alkali metal acetates, alkali metal bicarbonates, tri(lower alkyl) amines, and the like, for example, sodium acetate, potassium bicarbonate, triethylamine, and the like.

"Strong mineral base" refers to an inorganic, water-soluble base with a pK$_b$ less than about 6, such as sodium hydroxide, sodium carbonate, potassium carbonate, and the like.

Isolation and purification of the compounds and intermediates described herein can be effected, if desired, by any suitable separation or purification procedure such as, for example, filtration, extraction, crystallization, column chromatography, thin-layer chromatography, thick-layer (preparative) chromatography, distillation, or a combination of these procedures. Specific illustrations of suitable separation and isolation procedures can be had by references to the examples hereinbelow. However, other equivalent separation or isolation procedures can, of course, also be used.

Compounds of formula I are named and numbered as illustrated below. For example, a compound of formula I where R is ethyl and Ar is phenyl

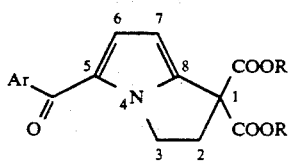

(I)

is named diethyl 5-benzoyl-2,3-dihydro-1H-pyrrolizine-1,1-dicarboxylate.

Synthesis of compounds of Formula I

Compounds of formula I may be prepared as described in greater detail below and illustrated in Reaction Scheme I.

Preparation of 2-Aroylpyrroles

The 2-aroylpyrroles can be prepared by the procedure of White, et al., *J. Org. Chem.*, 42, 4248 (1977) for the Vilsmeier-Haack aroylation of pyrroles utilizing aryl morpholide-acid chloride complexes or dialkylamine-acid chloride complexes. These reactions are further described in U.S. Pat. Nos. 4,353,829 (morpholides); and U.S. Pat. Nos. 4,089,969 and 4,347,186 (dialkylamides) for the preparation of aroyl pyrrolizines.

The aryl dialkylamides, aryl morpholides, aroyl halides, etc. are readily preparable by methods set forth in U.S. Pat. Nos. 4,353,829; 4,089,969; 4,347,186; 4,511,724; 4,533,671; and 4,536,512, all of which are incorporated herein by reference.

2-Aroylpyrroles may alternatively be prepared by the reaction of an aroyl halide and pyrrole.

Preparation of Compounds of Formula III, where X is Chloro

Compounds of formula III where X is chloro can be prepared by the procedure of Gonzalez, et al., *Can. J. Chem.*, 61, 1697 (1983). The nitrogen of the aroylpyrrole is alkylated via the reaction of an aroyl pyrrole, preferably 2-benzoylpyrrole or 2-(4-methoxybenzoyl)-pyrrole, with an excess of a 1,2-dihaloethane, preferably 1,2-dichloroethane in the presence of a molar equivalent of a phase transfer reagent, preferably tetrabutylammonium bromide and an excess of strong base, preferably aqueous sodium hydroxide. The solution is stirred at room temperature for 5 minutes to 16 hours, preferably 30 minutes. The organic layer is separated and the aqueous layer is washed with a polar solvent, such as methylene chloride. The organic layers are combined and concentrated under reduced pressure to afford crude product which can be purified by chromatography (e.g., on silica gel eluting with diethyl ether) to yield compounds of formula III where X is chloro, preferably 1-(2-chloroethyl)-2-benzoylpyrrole.

Preparation of Compounds of Formula III where X is Iodo or Bromo

A solution of a compound of formula III where X is chloro, preferably 1-(2-chloroethyl)-2-benzoylpyrrole, and an alkali metal salt, preferably sodium iodide or sodium bromide, in an aprotic solvent, such as acetonitrile, is heated at reflux until the reaction is complete. The solution is cooled and concentrated. The residue is taken up in a polar solvent, such as ethyl acetate. The organic solution is washed with water, dried, and concentrated under reduced pressure to afford crude product which can be purified by chromatography (e.g., silica gel eluting with ethyl acetate-hexane) to yield a compound of formula III where X is iodo or bromo, preferably 1-(2-iodoethyl)-2-benzoylpyrrole.

Preparation of Compounds of Formula III where X is Arenesulfonyloxy

A mixture of a compound of formula III where X is iodo, preferably 1-(2-iodoethyl)-2-benzoylpyrrole and silver p-toluenesulfonate in a polar aprotic solvent, preferably acetonitrile, is placed in a pressure bottle under an inert atmosphere, preferably nitrogen. The pressure bottle is heated, preferably at 120°–125° C., and shaken until the reaction is complete. The mixture is filtered, and the filtrate is concentrated under reduced pressure. The product, a compound of formula III where X is arenesulfonyloxy, preferably 1-(2-p-toluenesulfonyloxyethyl)-2-benzoylpyrrole, may be isolated by conventional means.

Preparation of Compounds of Formula IV

To a 0° C. solution of a di(lower alkyl) ester, preferably diethyl malonate, in a polar aprotic solvent, such as dimethylformamide, is added a strong base, preferably sodium hydride. The reaction mixture is warmed to room temperature. To this mixture is added a solution of a compound of formula III where X is bromo, iodo, or arenesulfonyloxy, preferably 1-(2-iodoethyl)-2-benzoylpyrrole, in an aprotic polar solvent, such as dimethylformamide. The reaction mixture is again stirred at room temperature for about 6 to 24 hours, preferably 16 hours. The reaction mixture is poured into water and extracted with a polar solvent, such as ethyl acetate. The organic layers are combined, washed with water and brine, dried, and concentrated under reduced pressure. The product, a compound of formula IV, preferably 2-benzoyl-[3,3-di(ethoxycarbonyl)propyl]pyrrole, may be isolated by conventional means.

Preparation of Compounds of Formula V

Compounds of formula V, i.e., 6,6-di(lower alkyl)-5,7-dioxaspiro[2.5]octane-4,8-diones, may be prepared according to the method of Singh, et al., *J. Org. Chem.*, 40, 2969 (1975) for 6,6-dimethyl-5,7-dioxaspiro[2.5]octane-4,8-dione. Other spiro cyclopropyl compounds may be prepared in a manner similar to that for 6,6-dimethyl-5,7-dioxaspiro[2.5]octane-4,8-dione, by substituting other ketones for acetone to form the dioxyketal ring. Thus, for example, 6,6-diethyl-5,7-dioxaspiro[2.5]octane-4,8-dione, 6-ethyl-6-methyl-5,7-dioxaspiro[2.5]octane-4,8-dione, and 6-methyl-6-propyl-5,7-dioxaspiro[2.5]octane-4,8-dione may be prepared using 3-pentanone, methyl ethyl ketone (2-butanone), and 2-pentanone, respectively. However, there is no particular advantage in varying the 6,6-substitution, since subsequent steps in the overall process remove these groups, and ease of removal is not enhanced by such variation, so that the 6,6-dimethyl compound is preferred.

Preparation of Compounds of Formula VI

This preparation is substantially that described in U.S. Pat. Nos. 4,347,186 and 4,873,340. The aroylpyrrole, preferably 2-benzoylpyrrole or 2-(4-methoxybenzoyl)pyrrole, is treated with an excess of an alkali metal hydride or other strong base, preferably sodium hydride in a polar aprotic solvent, such as dimethylformamide, under an inert atmosphere until the reaction is complete. To this mixture is then added a solution of a compound of formula V, preferably 6,6-dimethyl-5,7-dioxaspiro[2.5]octane-4,8-dione. The mixture is allowed to react for about 1-10 hours or until completion. The product, a compound of formula VI, preferably 2-benzoyl-1-[2,2-dimethyl-4,6-dioxo-1,3-dioxan-5-yl)ethyl]-pyrrole, can be isolated by conventional means.

Preparation of Compounds of Formula IV from Compounds of Formula VI

This preparation is substantially that given in U.S. Pat. Nos. 4,873,340 and 4,347,186. The cyclic diester, a compound of formula VI, preferably, 2-benzoyl-1-[2,2-dimethyl-4,6-dioxo-1,3-dioxan-5-yl)ethyl]pyrrole, is converted to the corresponding di(lower alkyl) dicarboxylate, a compound of formula IV, by treatment with a suitable alcohol in the presence of acid. In a preferred embodiment, a compound of formula VI is dissolved in ethanol, which had been previously saturated with hydrogen chloride, at 0°–20° C., for about 5 minutes to 5 hours, preferably 30 minutes to 3 hours. The diethyl ester or other di(lower alkyl) esters may then be recovered by conventional techniques to afford a compound of formula IV, preferably 2-benzoyl-[3,3-di(ethoxycarbonyl)-propyl]pyrrole.

Preparation of Compounds of Formula I from Compounds of Formula IV

Compounds of formula I may be produced via the reaction of a compound of formula IV with an electrochemical oxidant in the presence of a weak base and an alkanoic acid. "Electrochemical oxidant" refers to an agent providing to a reaction mixture an electrochemical potential exceeding 1 eV. The agent may either be an electrochemical cell containing the reaction mixture and having a voltage greater than 1 V between the electrodes; or may be a high valence metal ion, typically a transition metal ion in a higher oxidation state, having a redox potential greater than 1 eV. Examples of suitable high valence metal ions are Mn(III), e.g., as manganese(III) acetate, and Fe(III), e.g., as iron(III) perchlorate as described in the articles cited in the Background to the Invention. The high valence metal ion may be either added directly or generated in situ.

In a preferred embodiment, the high valence metal ion is a manganese(III) salt, preferably manganese(III) acetate. The manganese(III) salt may be added directly as manganese(III) acetate dihydrate or may be generated in situ from manganese(II). The procedure of Heiba, et al., *Org. Syn.*, 61, 22 (1983), wherein manganese(II) acetate tetrahydrate is oxidized with potassium permanganate, may be used to generated the manganese(III). An alternative procedure for generated manganese(III) involves a double redox cycle with manganese(II) acetate tetrahydrate, silver nitrate, and sodium persulfate. Additional procedures for producing high valence metal ions, and preferably manganese(III), in situ may also be used.

To a warm, preferably 60°–80° C., mixture of a high valence metal ion, preferably a manganese(III) salt, and more preferably manganese(III) acetate, in an alkanoic acid, preferably acetic acid, or a polar aprotic solvent such as acetonitrile, is added a weak base, preferably sodium acetate, and a compound of formula IV, preferably 2-benzoyl-[3,3-di(ethoxycarbonyl)propyl]pyrrole. The reaction is stirred, preferably at 50°–70° C. until the reaction is complete. The reaction mixture is diluted with a polar solvent, such as diethyl ether, and filtered. The resulting solution is washed with water and aqueous base, preferably 10% sodium hydroxide, dried, and concentrated under reduced pressure. The product, a compound of formula I, preferably diethyl 5-benzoyl-2,3-dihydro-1H-pyrrolizine-1,1-dicarboxylate, may be isolated by conventional means.

Preparation of Compounds of Formula VII

To a cold solution of a compound of formula IV, preferably 2-benzoyl-[3,3-di(ethoxycarbonyl)propyl]-pyrrole, in an aprotic polar solvent, such as tetrahydrofuran, is added a slight excess of a strong base, preferably sodium hydride. The reaction mixture is allowed to stir for about 30 minutes. To the reaction mixture is then added a halogenating agent, preferably N-bromosuccinimide. The reaction mixture is allowed to stir until complete The mixture is poured into water and extracted with an aprotic polar solvent, such as diethyl ether. The organic layers are combined, washed with water and brine, dried, and concentrated under reduced pressure. The residue may be purified by conventional means to produce a compound of formula VII, preferably 2-benzoyl-[3-bromo-3,3-di(ethoxycarbonyl)propyl]-pyrrole.

Preparation of Compounds of Formula I from Compounds of Formula VII

To a mixture of a compound of formula VII, preferably 2-benzoyl-[3-bromo-3,3-di(ethoxycarbonyl)propyl]-pyrrole, in a suitable solvent, is added an alkyl radical. A preferred alkyl radical, the methyl radical, is derived from the reaction of ferrous sulfate and hydrogen peroxide in dimethyl sulfoxide. In an alternative preferred embodiment, the alkyl radical is derived from a trialkylborane, preferably triethylborane, with oxygen (air) in a nonpolar solvent. The reaction mixture is allowed to stir until the reaction is complete. The reaction mixture is poured into water and extracted with a polar solvent, such as methylene chloride or diethyl ether. The combined organic extracts are washed, dried and concentrated under reduced pressure to yield a compound of formula I, preferably diethyl 5-benzoyl-2,3-dihydro-1H-pyrrolizine-1,1-dicarboxylate, which may be isolated by conventional means.

Preparation of Compounds of Formula II

A compound of formula I may be converted to the corresponding compound of formula II by the methods described in U.S. Pat. No. 4,347,186, which consist of treatment with base to accelerate ester hydrolysis, followed by treatment with acid to effect monodecarboxylation.

Preparation of salts of Compounds of Formula II

The salts of the carboxylic acids of compounds of formula II, in particular the tromethamine salts of these acids, may be prepared by conventional methods, such as those disclosed in U.S. Pat. No. 4,089,969.

Preferred Processes

A preferred process involves the preparation of compounds of formula I via the radical cyclization of compounds of formula IV. The cyclizations can be initiated by electrochemical oxidants, preferably high valence metal ions such as manganese(III) acetate.

Another preferred process involves the preparation of compounds of formula I via the radical cyclization of compounds of formula VII These cyclizations can be initiated by alkyl radicals.

Preferred Compounds

The preferred compounds are compounds of formula IV, preferably 2-benzoyl-[3,3-di(ethoxycarbonyl)-propyl]pyrrole, and compounds of formula VII, preferably 2-benzoyl-[3-bromo-3,3-di(ethoxycarbonyl)-propyl]pyrrole, which are useful as intermediates in the synthesis of compounds of formula II, such as 5-benzoyl-2,3-dihydro-1H-pyrrolizine-1-carboxylic acid, which are therapeutically useful as discussed hereinbefore.

EXAMPLES

The following preparations and examples are given to enable those skilled in the art to more clearly understand and to practice the present invention. The following preparations and examples illustrate this invention, but are not intended to limit its scope.

Preparation 1 preparation of 2-Aroylpyrroles

1A. 2-Benzoylpyrrole

To a solution of N,N-dimethylbenzamide (48.0 g, 0.32 mol) in 1,2-dichloroethane (500 mL) was added oxalyl chloride (48.0 g, 0.38 mol). The reaction mixture was stirred for 24 hours at room temperature. To the reaction mixture was then added pyrrole (22.0 g, 0.33 mol). The reaction mixture was again stirred for 24 hours at room temperature. Aqueous sodium acetate (20%, 200 mL) was added to the reaction mixture and vigorous stirring was continued for 24 hours at room temperature. The organic layer was filtered through a silica gel column and concentrated under reduced pressure to yield 2-benzoylpyrrole which was used without further purification. Yield 43.0 g (80%), mp 76°–77° C.

1B. Preparation of Other Aroylpyrroles

By following the procedure of part A above and substituting for N,N-dimethylbenzamide the following compounds:
N,N-dimethyl-4-methoxybenzamide,
N,N-dimethyl-4-methylthiobenzamide,
N,N-dimethyl-4-vinylbenzamide,
N,N-dimethyl-2,4-dichlorobenzamide,
N,N-dimethyl-3-methylbenzamide,
N,N-dimethyl-2-furoylamide,
N,N-dimethyl-2-thenoylamide,
N,N-dimethyl-3-thenoylamide,
N,N-dimethyl-3-ethyl-2-thenoylamide,
N,N-dimethyl-4-n-butyl-2-furoylamide, or
N,N-dimethyl-1-methyl-2-pyrroylamide;
there are obtained the following compounds:
2-(4-methoxybenzoyl)pyrrole,
2-(4-methylthiobenzoyl)pyrrole,
2-(4-vinylbenzoyl)pyrrole,
2-(2,4-dichlorobenzoyl)pyrrole,
2-(3-methylbenzoyl)pyrrole,
2-(2-furoyl)pyrrole,
2-(2-thenoyl)pyrrole,
2-(3-thenoyl)pyrrole,
2-(3-ethyl-2-thenoyl)pyrrole,
2-(4-n-butyl-2-furoyl)pyrrole, and
2-(1-methyl-2-pyrroyl)pyrrole.

1C. Preparation of Additional Aroylpyrroles

By following the procedures of U.S. Pat. Nos. 4,089,969 and 4,353,829 and substituting other N,N-dialkylarylamides or arylmorpholides for N,N-dimethylbenzamide, additional 2-aroylpyrroles may be obtained.

EXAMPLE 1

Preparation of Compounds of Formula III

1A. A Compound of Formula III where X is Chloro, 1-(2-Chlorethyl)-2-benzoylpyrrole To a solution of 2-benzoylpyrrole (9.40 g, 55 mmol) and tetrabutylammonium bromide (17.7 g, 55 mmol) in 1,2-dichloroethane (200 mL) was added cold aqueous sodium hydroxide (0° C, 50 mL, 50%). The reaction mixture was stirred at room temperature for 30 minutes. The organic layer was separated and the aqueous layer was washed with methylene chloride (3×200 mL). The organic layers were combined and concentrated under reduced pressure. The crude product, 1-(2-chloroethyl)-2-benzoylpyrrole, was purified by column chromatography on silica gel eluting with diethyl ether. Yield 11.4 g (89%), mp 54°–55° C.

1B. A Compound of Formula III where X is Iodo, 1-(2-Iodoethyl)-2-benzoylpyrrole A solution of 1-(2-chloroethyl)-2-benzoylpyrrole (11.4 g, 49.0 mmol) and sodium iodide (14.7 g, 98.0 mmol) in acetonitrile (250 mL) was refluxed for 1 day. The solution was cooled and concentrated under reduced pressure. The residue was taken up in ethyl acetate (500 mL), washed with water (300 mL), and concentrated. The crude product, 1-(2-iodoethyl)-2-benzoylpyrrole, was purified by column chromatography on silica gel. Yield 12.7 g (80%).

1C. Other Compounds of Formula III Where X is Iodo

By following the procedure of part B above and substituting for 1-(2-chloroethyl)-2-benzoylpyrrole, the following compounds:
1-(2-chloroethyl)-2-(4-methoxybenzoyl)pyrrole,
1-(2-chloroethyl)-2-(4-methylthiobenzoyl)pyrrole,
1-(2-chloroethyl)-2-(4-vinylbenzoyl)pyrrole,
1-(2-chloroethyl)-2-(2,4-dichlorobenzoyl)pyrrole,
1-(2-chloroethyl)-2-(3-methylbenzoyl)pyrrole,
1-(2-chloroethyl)-2-(2-furoyl)pyrrole,
1-(2-chloroethyl)-2-(2-thenoyl)pyrrole,
1-(2-chloroethyl)-2-(3-thenoyl)pyrrole,
1-(2-chloroethyl)-2-)3-ethyl-2-thenoyl)pyrrole,
1-(2-chloroethyl)-2-(4-n-butyl-2-furoyl)pyrrole, and
1-(2-chloroethyl)-2-(1-methyl-2-pyrroyl)pyrrole,
there are obtained the following compounds:
1-(2-iodoethyl)-2-(4-methoxybenzoyl)pyrrole,
1-(2-iodoethyl)-2-(4-methylthiobenzoyl)pyrrole,
1-(2-iodoethyl)-2-(4-vinylbenzoyl)pyrrole,
1-(2-iodoethyl)-2-(2,4-dichlorobenzoyl)pyrrole,
1-(2-iodoethyl)-2-(3-methylbenzoyl)pyrrole,
1-(2-iodoethyl)-2-(2-furoyl)pyrrole,
1-(2-iodoethyl)-2-(2-thenoyl)pyrrole,
1-(2-iodoethyl)-2-(3-thenoyl)pyrrole,
1-(2-iodoethyl)-2-(3-ethyl-2-thenoyl)pyrrole,
1-(2-iodoethyl)-2-(4-n-butyl-2-furoyl)pyrrole, and
1-(2-iodoethyl)-2-(1-methyl-2-pyrroyl)pyrrole,

1D. Other Compounds of Formula III Where X is Bromo

By following the procedure of parts B and C above and substituting sodium bromide for sodium iodide; there are obtained the following compounds:
1-(2-bromoethyl)-2-(4-methoxybenzoyl)pyrrole,
1-(2-bromoethyl)-2-(4-methylthiobenzoyl)pyrrole,
1-(2-bromoethyl)-2-(4-vinylbenzoyl)pyrrole,
1-(2-bromoethyl)-2-(2,4-dichlorobenzoyl)pyrrole,
1-(2-bromoethyl)-2-(3-methylbenzoyl)pyrrole,
1-(2-bromoethyl)-2-(2-furoyl)pyrrole,
1-(2-bromoethyl)-2-(2-thenoyl)pyrrole,
1-(2-bromoethyl)-2-(3-thenoyl)pyrrole,
1-(2-bromoethyl)-2-)3-ethyl-2-thenoyl)pyrrole,
1-(2-bromoethyl)-2-(4-n-butyl-2-furoyl)pyrrole, and
1-(2-bromoethyl)-2-(1-methyl-2-pyrroyl)pyrrole.

1E. Compounds of Formula III Where X is Arenesulfonyloxy

A mixture of 1-(2-iodoethyl)-2-benzoylpyrrole (100 mg, 0.31 mmol) and silver p-toluenesulfonate (1.45 g, 5.21 mmol) in acetonitrile (20 mL) is placed in a pressure bottle. The pressure bottle is purged with nitrogen, heated to 120°–125° C., and shaken until the reaction is complete. The reaction mixture is filtered and the filtrate is concentrated under reduced pressure. The residue is purified by column chromatography on silica gel to give 1-(2-p-toluenesulfonyloxy)-2-benzoylpyrrole.

1F. Other Compounds of Formula III where X is Arenesulfonyloxy

By following the procedure of part E above and substituting other 1-(2-iodoethyl)-2-aroylpyrroles for 1-(2-iodoethyl)-2-benzoylpyrrole, there are obtained the corresponding 1-(2-p-toluenesulfonyloxy)-2-aroylpyrroles.

EXAMPLE 2

Preparation of Compounds of Formula IV

2A. A Compound of Formula IV, 2-Benzoyl-[3,3-di(ethoxycarbonyl)propyl]pyrrole, from the Alkylation of a Compound of Formula III To a solution of diethyl malonate (5.40 g, 33.8 mmol) in anhydrous N,N-dimethylformamide (50 mL) at 0° C. was added sodium hydride (60% in mineral oil, 1.35 g, 33.8 mmol). The reaction mixture was warmed and stirred at room temperature for 30 minutes. To this mixture was then added a solution of 1-(2-iodoethyl)-2-benzoylpyrrole (11.0 g, 33.8 mmol) in N,N-dimethylformamide (50 mL). The reaction mixture was stirred at room temperature for 16 hours. The mixture was poured into water (1000 mL) and extracted with ethyl acetate (3×300 mL). The ethyl acetate extracts were combined, washed with water (2×200 mL) and saturated aqueous sodium chloride (300 mL), dried (Na$_2$SO$_4$), and concentrated under reduced pressure. The crude oil was purified by column chromatography on silica gel eluting with hexane/ethyl acetate to provide 9.85 g (82%) of 2-benzoyl-1-[3,3-di(ethoxycarbonyl)propyl]pyrrole.

2B. Other Compounds of Formula IV

By following the procedure of part A above and substituting for 1-(2-iodoethyl)-2-benzoylpyrrole, other 1-(2-iodoethyl)-2-aroylpyroles such as the following compounds:
1-(2-iodoethyl)-2-(4-methoxybenzoyl)pyrrole,
2-(2-iodoethyl)-2-(4-methylthiobenzoyl)pyrrole,
1-(2-iodoethyl)-2-(4-vinylbenzoyl)pyrrole,
1-(2-iodoethyl)-2-(2,4-dichlorobenzoyl)pyrrole,
1-(2-iodoethyl)-2-(3-methylbenzoyl)pyrrole,
1-(2-iodoethyl)-2-(2-furoyl)pyrrole,
1-(2-iodoethyl)-2-(2-thenoyl)pyrrole,
1-(2-iodoethyl)-2-(3-thenoyl)pyrrole,
1-(2-iodoethyl)-2-(3-ethyl-2-thenoyl)pyrrole,
1-(2-iodoethyl)-2-(4-n-butyl-2-furoyl)pyrrole, and 1-(2-iodoethyl)-2-(1-methyl-2-pyrroyl)pyrrole, there are obtained the following compounds:

2-(4-methoxybenzoyl)-1-[3,3-di(ethoxycarbonyl)propyl]pyrrole,
2-(4-methylthiobenzoyl)-1-[3,3-di(ethoxycarbonyl)propyl]pyrrole,
2-(4-vinylbenzoyl)-1-[3,3-di(ethoxycarbonyl)propyl]pyrrole,
2-(2,4-dichlorobenzoyl)-1-[3,3-di(ethoxycarbonyl)propyl]pyrrole,
2-(3-methylbenzoyl)-1-[3,3-di(ethoxycarbonyl)propyl]pyrrole,
2-(2-furoyl)-1-[3,3-di(ethoxycarbonyl)propyl]pyrrole,
2-(2-thenoyl)-1-[3,3-di(ethoxycarbonyl)propyl]pyrrole,
2-(3-thenoyl)-1-[3,3-di(ethoxycarbonyl)propyl]pyrrole,
2-(3-ethyl-2-thenoyl)-1-[3,3-di(ethoxycarbonyl)propyl]pyrrole,
2-(4-n-butyl-2-furoyl)-1-[3,3-di(ethoxycarbonyl)propyl]pyrrole, and
2-(1-methyl-2-pyrroyl)-1-[3,3-di(ethoxycarbonyl)propyl]pyrrole.

2C. Additional Compounds of Formula IV

By following the procedures of parts A and B above, and substituting other 1-(2-bromoethyl)-2-aroylpyrroles for 1-(2-iodoethyl)-2-benzoylpyrrole, there are obtained other 2-aroyl-1-[3,3-di(ethoxycarbonyl)propyl]pyrroles.

2D. Additional Compounds of Formula IV

By following the procedures of parts A and B above, and substituting other 1-(2-arenesulfonyloxy)-2-aroylpyrroles for 1-(2-iodoethyl)-2-benzoylpyrrole, there are obtained other 2-aroyl-1-[3,3-di(ethoxycarbonyl)propyl]pyrroles.

2E. Other Esters of Formula IV

By following the procedure of part A above and substituting other di(lower alkyl) esters for diethyl malonate, there are obtained the corresponding 2-aroyl-1-[3,3-di(lower alkoxycarbonyl)propyl]pyrrole.

EXAMPLE 3

Preparation of Compounds of Formula VI

3A. A Compound of Formula VI, 2-Benzoyl-1-[2-(2,2-dimethyl-4,6-dioxo-1,3-dioxan-5yl-)ethyl]pyrrole To a solution of 2-benzoylpyrrole (730 mg, 4.3 mmol) in anhydrous dimethylformamide (10 mL) was added sodium hydride (60% in mineral oil, 172 mg, 4.3 mmol). The reaction mixture was allowed to stir for one hour at room temperature. To the reaction mixture was then added, in one portion, 6,6-dimethyl-5,7-dioxaspiro[2.5]octane-4,8-dione (730 mg, 4.3 mmol). The reaction temperature was raised to 70°-80° C. and the reaction was allowed to continue for 6 hours. The mixture as cooled, poured into diethyl ether (100 mL), stirred for one hour, and filtered. The precipitate was washed with diethyl ether and dried under reduced pressure to yield the sodium salt of 2-benzoyl-1-[2-(2,2-dimethyl-4,6-dioxo-1,3-dioxan-5-yl)ethyl]pyrrole which was used without further purification.

3B. Other Compounds of Formula VI

By following the procedure of part A above and substituting for 2-benzoylpyrrole, the following compounds:
2-(4-methoxybenzoyl)pyrrole,
2-(4-methylthiobenzoyl)pyrrole,
2-(4-vinylbenzoyl)pyrrole,
2-(2,4-dichlorobenzoyl)pyrrole,
2-(3-methylbenzoyl)pyrrole,
2-(2-furoyl)pyrrole,
2-(2-thenoyl)pyrrole,
2-(3-thenoyl)pyrrole,
2-(3-ethyl-2-thenoyl)pyrrole,
2-(4-n-butyl-2-furoyl)pyrrole, and
2-(1-methyl-2-pyrroyl)pyrrole;
there are obtained the following compounds:
2-(4-methoxybenzoyl)-1-[2-(2,2-dimethyl-4,6-dioxo-1,3-dioxan-5-yl)ethyl]pyrrole,
2-(4-methylthiobenzoyl)-1-[2-(2,2-dimethyl-4,6-dioxo-1,3-dioxan-5-yl)ethyl]pyrrole,
2-(4-vinylbenzoyl)-1-[2-(2,2-dimethyl-4,6-dioxo-1,3-dioxan-5-yl)ethyl]pyrrole,
2-(2,4-dichlorobenzoyl)-1-[2-(2,2-dimethyl-4,6-dioxo-1,3-dioxan-5-yl)ethyl]pyrrole,
2-(3-methylbenzoyl)-1-[2-(2,2-dimethyl-4,6-dioxo-1,3-dioxan-5-yl)ethyl]pyrrole,
2-(2-furoyl)-1-[2-(2,2-dimethyl-4,6-dioxo-1,3-dioxan-5-yl)ethyl]pyrrole,
2-(2-thenoyl)-1-[2-(2,2-dimethyl-4,6-dioxo-1,3-dioxan-5-yl)ethyl]pyrrole,
2-(3-thenoyl)-1-[2-(2,2-dimethyl-4,6-dioxo-1,3-dioxan-5-yl)ethyl]pyrrole,
2-(3-ethyl-2-thenoyl)-1-[2-(2,2-dimethyl- 4,6-dioxo-1,3-dioxan-5-yl)ethyl]pyrrole,
2-(4-n-butyl-2-furoyl)-1-[2-(2,2-dimethyl-4,6-dioxo-1,3-dioxan-5-yl)ethyl]pyrrole, or
2-(1-methyl-2-pyrroyl)-1-[2-(2,2-dimethyl-4,6-dioxo-1,3-dioxan-5-yl)ethyl]pyrrole.

EXAMPLE 4

Preparation of Compounds of Formula IV

4A. A Compound of Formula IV, 2-Benzoyl-1-[3,3-di(methoxycarbonyl)propyl]pyrrole, via the Hydrolysis of a Compound of Formula VI To a 0° C. solution of methanol (10 mL) which had been saturated with gaseous hydrogen chloride was added a solution of the sodium salt of 2-benzoyl-1-[2-(2,2-dimethyl-4,6-dioxo-1,3-dioxan-5-yl)ethyl]pyrrole (1.41 g, 3.9 mmol) in methanol (10 mL). The mixture was stirred for sixteen hours at room temperature and was then concentrated under reduced pressure. The residue was purified by chromato-graphy on silica eluting with hexane/ethyl acetate (70:30) to yield 530 mg (42%) of 2-benzoyl-1-[3,3-di(methoxycarbonyl)propyl]pyrrole.

4B. Other Compounds of Formula IV

By following the procedure of part A above and substituting for 2-(benzoyl)-1-[2-(2,2-dimethyl-4,6-dioxo-1,3-dioxan-5-yl)ethyl]pyrrole, the following compounds:
2-(4-methoxybenzoyl)-1-[2-(2,2-dimethyl-4,6-dioxo-1,3-dioxan-5-yl)ethyl]pyrrole,
2-(4-methylthiobenzoyl)-1-[2-(2,2-dimethyl-4,6-dioxo-1,3-dioxan-5-yl)ethyl]pyrrole, 2-(4-vinylbenzoyl)-1-[2-(2,2-dimethyl-4,6-dioxo-1,3-dioxan-5-yl)ethyl]pyrrole,
2-(2,4-dichlorobenzoyl)-1-[2-(2,2-dimethyl-4,6-dioxo-1,3-dioxan-5-yl)ethyl]pyrrole,
2-(3-methylbenzoyl)-1-[2-(2,2-dimethyl-4,6-dioxo-1,3-dioxan-5-yl)ethyl]pyrrole,
2-(2-furoyl)-1-[2-(2,2-dimethyl-4,6-dioxo-1,3-dioxan-5-yl)ethyl]pyrrole,
2-(2-thenoyl)-1-[2-(2,2-dimethyl-4,6-dioxo-1,3-dioxan-5-yl)ethyl]pyrrole,
2-(3-thenoyl)-1-[2-(2,2-dimethyl-4,6-dioxo-1,3-dioxan-5-yl)ethyl]pyrrole,
2-(3-ethyl-2-thenoyl)-1-[2-(2,2-dimethyl-4,6-dioxo-1,3-dioxan-5-yl)ethyl]pyrrole,
2-(4-n-butyl-2-furoyl)-1-[2-(2,2-dimethyl-4,6-dioxo-1,3-dioxan-5-yl)ethyl]pyrrole, and
2-(1-methyl-2-pyrroyl)-1-[2-(2,2-dimethyl-4,6-dioxo-1,3-dioxan-5-yl)ethyl]pyrrole;
there are obtained the following compounds:
2-(4-methoxybenzoyl)-1-[3,3-di(methoxycarbonyl)propyl]pyrrole,
2-(4-methylthiobenzoyl)-1-[3,3-di(methoxycarbonyl)propyl]pyrrole,
2-(4-vinylbenzoyl)-1-[3,3-di(methoxycarbonyl)propyl]pyrrole,
2-(2,4-dichlorobenzoyl)-1-[3,3-di(methoxycarbonyl)propyl]pyrrole,
2-(3-methylbenzoyl)-1-[3,3-di(methoxycarbonyl)propyl]pyrrole,
2-(2-furoyl)-1-[3,3-di(methoxycarbonyl)propyl]pyrrole,
2-(2-thenoyl)-1-[3,3-di(methoxycarbonyl)propyl]pyrrole,
2-(3-thenoyl)-1-[3,3-di(methoxycarbonyl)propyl]pyrrole,
2-(3-ethyl-2-thenoyl)-1-[3,3-di(methoxycarbonyl)propyl]pyrrole,
2-(4-n-butyl-2-furoyl)-1-[3,3-di(methoxycarbonyl)propyl]pyrrole, and
2-(1-methyl-2-pyrroyl)-1-[3,3-di(methoxycarbonyl)propyl]pyrrole.

4C. Other Esters of Formula IV

By following the procedures of parts A and B above and substituting other lower alkyl alcohols for the methanol, there are obtained other 2-aroyl-1-[3,3-di(lower alkoxycarbonyl)propyl]pyrroles.

EXAMPLE 5

Preparation of Compounds of Formula I

5A. A Compound of Formula I, Diethyl 5-benzoyl-2,3-dihydro-1H-pyrrolizine-1,1-dicarboxylate To a solution of 2-benzoyl-1-[3,3-di(ethoxycarbonyl)propyl]pyrrole (1.00 g, 2.80 mmol) and anhydrous sodium acetate (4.60 mg, 5.6 mmol) in acetic acid (20 mL) is added manganese(III) acetate dihydrate (2.25 g, 8.4 mmol) The mixture was stirred for two hours at 80° C. The reaction mixture was diluted with diethyl ether (100 mL), and filtered. The resulting solution was washed with water (2×25 mL), 10% sodium hydroxide (2×30 mL), and water (2×25 mL), dried (Na2SO4) and concentrated under reduced pressure. The crude oil was purified by flash chromatography on silica eluting with hexane/ethyl acetate (90:10-80:20) to yield 800 mg (80%) of diethyl 5-benzoyl-2,3-dihydro-1H-pyrrolizine-1,1-dicarboxylate.

5B. Alternative Preparation of a Compound of Formula I using Mn(II) Acetate and Potassium Permanganate To a hot (80° C.) solution of manganese(II) acetate tetrahydrate (858 mg, 3.50 mmol) in acetic acid (8 mL) were added sequentially potassium permanganate (138 mg, 0.875 mmol), acetic anhydride (1,355 mg, 10.5 mmol), anhydrous sodium acetate (420 mg, 5 mmol) and a solution of 2-benzoyl-1-[3,3-di(ethoxycarbonyl)propyl]pyrrole (500 mg, 1.40 mmol) in acetic acid (2 mL). The resulting mixture was stirred at 80° C. for 6 hours, cooled, poured into water (25 mL), and extracted with toluene (3×25 mL). The combined toluene extracts were washed with water (25 mL) and concentrated under reduced pressure to provide 478 mg (96%) of diethyl 5-benzoyl-2,3-dihydro-1H-pyrrolizine-1,1-dicarboxylate (I).

5C. Alternate Preparation of a Compound of Formula I using Mn(II) Acetate, Silver Nitrate and Sodium Persulfate A mixture of manganese(II) acetate tetrahydrate (343 mg, 1.40 mmol), silver nitrate (23.8 mg, 0.140 mmol), sodium acetate (420 mg, 5 mmol), acetic anhydride (542 mg, 4.20 mmol) and sodium persulfate (333 mg, 1.4 mmol) in acetic acid (8 mL) was stirred at 80° C. for 30 minutes. To this mixture was added a solution of 2-benzoyl-1-[3,3-di(ethoxycarbonyl)propyl]pyrrole (500 mg, 1.40 mmol) in acetic acid (2 mL). To the reaction mixture was then added additional sodium persulfate (333 mg, 1.4 mmol). The resulting mixture was stirred at 80° C. for 12 hours, cooled, poured into water (25 mL), and extracted with toluene (3×25 mL). The combined toluene extracts were washed with water (25 mL) and concentrated under reduced pressure, providing 475 mg (95%) of diethyl 5-benzoyl-2,3-dihydro-1H-pyrrolizine-1,1-dicarboxylate.

5D. Other Compounds of Formula I

By following the procedure of parts A, B, or C above and substituting for 2-benzoyl-1-[3,3-di(ethoxycarbonyl)propyl]pyrrole, the following compounds:
2-(4-methoxybenzoyl)-1-[3,3-di(ethoxycarbonyl)propyl]pyrrole,
2-(4-methylthiobenzoyl)-1-[3,3-di(ethoxycarbonyl)propyl]pyrrole,
2-(4-vinylbenzoyl)-1-[3,3-di(ethoxycarbonyl)propyl]pyrrole,
2-(2,4-dichlorobenzoyl)-1-[3,3-di(ethoxycarbonyl)propyl]pyrrole,
2-(3-methylbenzoyl)-1-[3,3-di(ethoxycarbonyl)propyl]pyrrole,
2-(2-furoyl)-1-[3,3-di(ethoxycarbonyl)propyl]pyrrole,
2-(2-thenoyl)-1-[3,3-di(ethoxycarbonyl)propyl]pyrrole,
2-(3-thenoyl)-1-[3,3-di(ethoxycarbonyl)propyl]pyrrole,
2-(3-ethyl-2-thenoyl)-1-[3,3-di(ethoxycarbonyl)propyl]pyrrole,
2-(4-n-butyl-2-furoyl)-1-[3,3-di(ethoxycarbonyl)propyl]pyrrole, and
2-(1-methyl-2-pyrroyl)-1-[3,3-di(ethoxycarbonyl)propyl]pyrrole;
there are obtained the following compounds:
diethyl 5-(4-ethoxybenzoyl)-3,4-dihydro-1H-pyrrolizine-1,1-dicarboxylate,
diethyl 5-(4-methylthiobenzoyl)-3,4-dihydro-1H-pyrrolizine-1,1-dicarboxylate,
diethyl 5-(4-vinylbenzoyl)-3,4-dihydro-1H-pyrrolizine-1,1-dicarboxylate, diethyl 5-(2,4-dichlorobenzoyl)-3,4-dihydro-1H pyrrolizine-1,1-dicarboxylate,
diethyl 5-(3-methylbenzoyl)-3,4-dihydro-1H pyrrolizine-1,1-dicarboxylate, diethyl 5-(2-furoyl)-3,4-dihydro-1H-pyrrolizine-1,1-dicarboxylate,
diethyl 5-(2-thenoyl)-2,3-dihydro-1H-pyrrolizine-pyrrole-1,1-dicarboxylate,
diethyl 5-(3-thenoyl)-2,3-dihydro-1H-pyrrolizine-pyrrole-1,1-dicarboxylate,
diethyl 5-(3-ethyl-2-thenoyl)-2,3-dihydro-1H-pyrrolizine-1,1-dicarboxylate,
diethyl 5-(4-n-butyl-2-furoyl)-2,3-dihydro-1H-pyrrolizine-1,1-dicarboxylate, and
diethyl 5-(1-methyl-2-pyrroyl)-2,3-dihydro-1H-pyrrolizine-1,1-dicarboxylate,

EXAMPLE 6

Preparation of Compounds of Formula VII

6A. A Compound of Formula VII where Y is Bromo, 2-Benzoyl-[3-bromo-3,3-di(ethoxycarbonyl)propyl]pyrrole To a solution of 2-benzoyl-1-[3,3-di(ethoxycarbonyl)propyl]pyrrole (1.12 g, 3.14 mmol) in tetrahydrofuran (50 mL) at 0° C. was slowly added sodium hydride (60% in mineral oil, 0.14 g, 3.45 mmol). The reaction mixture was allowed to stir for 30 minutes. To the reaction mixture was then added N-bromosuccinimide (0.64 g, 3.45 mmol). The reaction mixture was allowed to stir for an additional 30 minutes. The mixture was poured into water (200 mL) and extracted with diethyl ether (3×100 mL). The organic layers were combined, washed with water (100 mL) and saturated aqueous sodium chloride solution (100 mL), dried ($Na_2SO_4$), and concentrated under reduced pressure. The residue was purified by chromatography on silica eluting with hexane/ethyl acetate (90:10) to yield 1.15 q (84%) of 2-benzoyl-[3-bromo-3,3-di(ethoxycarbonyl)propyl]pyrrole.

6B. Other Compounds of Formula VII where Y is Bromo

By following the procedure of part A above and substituting other 2-aroyl-1-[3,3-di(lower alkoxycarbonyl)propyl]pyrroles for 2-benzoyl-1-[3,3-di(ethoxycarbonyl)propyl]pyrrole, there are obtained the corresponding 2-aroyl-[3-bromo-3,3-di(lower alkoxycarbonyl)propyl]pyrroles.

6C. Compounds of Formula VII where Y is Iodo

By following the procedure of part A above and substituting iodine for N-bromosuccinimide, there are obtained the corresponding 2-aroyl-[3-iodo-3,3-di(lower alkoxycarbonyl)propyl]pyrroles.

EXAMPLE 7

Alternative Preparations of Compounds of Formula I

7A. Preparation of a Compound of Formula I, Diethyl 5-Benzoyl-2,3-dihydro-1H-pyrrolizine-1,1-dicarboxylate, using Fe(II) Sulfate, Hydrogen Peroxide, Dimethyl Sulfoxide, and a Compound of Formula VII To a solution of a 2-benzoyl-[3-bromo-3,3-di(ethoxycarbonyl)propyl]pyrrole (715 mg, 1.64 mmol) and iron(II) sulfate heptahydrate (456 mg, 1.64 mmol) in dimethyl sulfoxide (25 mL) was added in a dropwise manner cold hydrogen peroxide (30%, 1.67 mL, 16.4 mmol). The reaction mixture was poured into water and extracted with methylene chloride. The combined organic layers were washed with saturated sodium bicarbonate solution, dried, and concentrated under reduced pressure. The residue was purified by chromatography on silica gel eluting with hexane/ethyl acetate (85:15) to provide 290 mg (50%) of diethyl 5-benzoyl-2,3-dihydro-1H-pyrrolizine-1,1-dicarboxylate.

7B. Preparation of a Compound of Formula I using Triethylborane, Oxygen, and a Compound of Formula VII To a solution of 2-benzoyl-[3-bromo-3,3-di(ethoxycarbonyl)propyl]pyrrole (436 mg, 1.0 mmol) in benzene (20 mL) was added triethylborane (1.0M in hexane, 5 mL, 5 mmol). The reaction mixture was stirred in an open vessel for one hour. Additional triethylborane (1 mL, 1 mmol) was added and the reaction was allowed to stir in an open vessel for an additional hour. The reaction mixture was poured into water and extracted with diethyl ether. The combined organic layers were washed with saturated aqueous sodium chloride, dried ($Na_2SO_4$), and concentrated under reduced pressure. The residue was purified by chromatography on silica gel eluting with hexane/ethyl acetate (85:15) to provide 266 mg (75%) of diethyl 5-benzoyl-2,3-dihydro-1H-pyrrolizine-1,1-dicarboxylate.

7C. Other Compounds of Formula I

By following the procedure of part A or B above and substituting other 2-aroyl-[3-halo-3,3-di(lower alkoxycarbonyl)propyl]pyrroles for 2-benzoyl-[3-bromo-3,3-di(ethoxycarbonyl)propyl]pyrrole, there are obtained the corresponding di(lower alkyl) 5-aroyl-2,3-dihydro-1H-pyrrolizine-1,1-dicarboxylates.

EXAMPLE 8

Preparation of Compounds of Formula II

8A. A Compound of Formula II, 5-(4-Benzoyl)-2,3-dihydro-1H-pyrrolizine-1-carboxylic acid A mixture of diethyl 5-benzoyl-2,3-dihydro-1H-pyrrolizine-1,1-dicarboxylate (600 mg, 1.69 mmol) in diethyl ether and 20% aqueous sodium hydroxide (10 mL) was refluxed with vigorous stirring for 24 hours. The aqueous layer was washed with ether (20 mL), and acidified with concentrated hydrochloric acid. The aqueous layer was washed with ethyl acetate (3×20 mL). The ethyl acetate extracts were combined and warmed at 70° C. for 4 hours. The ethyl acetate solution was concentrated under reduced pressure to yield 400 mg (93%) of 5-benzoyl-2,3-dihydro-1H-pyrrolizine-1-carboxylic acid (ketorolac).

8B. Other Compounds of Formula II

By following the procedure of part A above and substituting other substituted pyrrolizine-1,1-dicarboxylates for diethyl 5-benzoyl-2,3-dihydro-1H-pyrrolizine-1,1-dicarboxylate, there are obtained the corresponding 5-benzoyl-2,3-dihydro-1H-pyrrolizine-1-carboxylic acid.

EXAMPLE 9

Preparation of Salts of Compounds of Formula II

9A. Preparation of the Tromethamine Salt of Compounds of Formula II

To a warm solution of 5-benzoyl-2,3-dihydro-1H-pyrrolizine-1-carboxylic acid (200 mg, 0.78 mmol) in 15 mL of benzene was added tromethamine (60 mg, 0.78 mmol). The reaction mixture was cooled and filtered. The precipitate was washed with ether and dried to yield the tromethamine salt of 5-benzoyl-2,3-dihydro-1H-pyrrolizine-1-carboxylic acid.

9B. Preparation of Other Salts of Compounds of Formula II

In similar manner, the compounds of formula II can be converted to their corresponding pharmaceutically acceptable salts by treatment with the appropriate base, for example, diethylamine, ethanolamine, piperidine, isopropylamine, choline, caffeine and the like.

We claim:

1. A process for producing a compound of formula

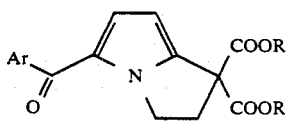
(I)

in which each R is independently lower alkyl and Ar is aryl, which comprises treating a compound of formula IV,

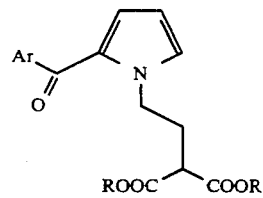
(IV)

in which
R and Ar are defined as above,
with a high valence metal ion in an alkanoic acid or polar aprotic solvent.

2. The process of claim 1 wherein Ar is selected from 4-(R"W)-phenyls.

3. The process of claim 1 wherein Ar is phenyl and R is ethyl.

4. A compound of formula IV,

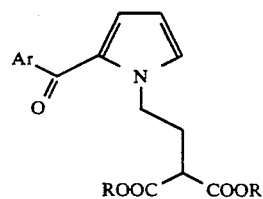
(IV)

in which
each R is independently lower alkyl; and Ar is aryl.

5. A compound of claim 4 wherein Ar is selected from 4-(R"W)-phenyls.

6. A compound of claim 4 wherein Ar is phenyl and R is ethyl.

7. The process of claim 1 wherein the high valence metal ion is a transition metal ion in a higher valence state.

8. The process of claim 7 wherein the transition metal ion is selected from manganese(III) and iron(III).

9. The process of claim 8 wherein the transition metal ion is manganese(III).

10. The process of claim 1 wherein the high valence metal ion is generated in situ.

11. The process of claim 10 wherein the high valence metal ion is a transition metal ion in a higher valence state.

12. The process of claim 11 wherein the transition metal ion is selected from manganese(III) and iron(III).

13. The process of claim 12 wherein the transition metal ion is manganese(III).

* * * * *

UNITED STATES PATENT AND TRADEMARK OFFICE
CERTIFICATE OF CORRECTION

PATENT NO. : 5,082,951

DATED : January 21, 1992

INVENTOR(S) : Joseph M. Muchowski et al.

It is certified that error appears in the above-identified patent and that said Letters Patent is hereby corrected as shown below:

Column 24,

Claim 2, line 2, delete the period and insert therefor:
-- wherein R" is hydrogen, fluoro, chloro, bromo or nitro, or lower alkyl, lower alkenyl, or lower alkynyl, optionally substituted by halogen; W is a covalent bond,-O-,-S-,-S(O)-,-S(O)$_2$-,-NR-,-CHR-, where R is alkyl; except that if R" is nitro, fluoro, chloro, or bromo, then W is a covalent bond.--

Column 24,

Claim 5, line 2, delete the period and insert therefor:
-- wherein R" is hydrogen, fluoro, chloro, bromo or nitro, or lower alkyl, lower alkenyl, or lower alkynyl, optionally substituted by halogen; W is a covalent bond,-O-,-S-,-S(O)-,-S(O)$_2$-,-NR-,-CHR-, where R is alkyl; except that if R" is nitro, fluoro, chloro, or bromo, then W is a covalent bond.--

Signed and Sealed this

Twentieth Day of April, 1993

*Attest:*

MICHAEL K. KIRK

*Attesting Officer*   Acting Commissioner of Patents and Trademarks